United States Patent
Chang et al.

(10) Patent No.: US 10,937,163 B2
(45) Date of Patent: Mar. 2, 2021

(54) IMAGE CAPTURING DEVICE

(71) Applicant: QUANTA COMPUTER INC., Taoyuan (TW)

(72) Inventors: Jung-Wen Chang, Taoyuan (TW); Chien-Hung Lin, Taoyuan (TW)

(73) Assignee: QUANTA COMPUTER INC.

( * ) Notice: Subject to any disclaimer, the term of this patent is extended or adjusted under 35 U.S.C. 154(b) by 116 days.

(21) Appl. No.: 16/185,967

(22) Filed: Nov. 9, 2018

(65) Prior Publication Data

US 2019/0370968 A1 Dec. 5, 2019

(30) Foreign Application Priority Data

Jun. 1, 2018 (TW) ................... 107118968

(51) Int. Cl.
*G06T 7/00* (2017.01)
*H04N 5/225* (2006.01)
*H04N 5/235* (2006.01)
*G06T 5/50* (2006.01)

(52) U.S. Cl.
CPC .............. *G06T 7/0014* (2013.01); *G06T 5/50* (2013.01); *H04N 5/2256* (2013.01); *H04N 5/2352* (2013.01); *G06T 2207/10152* (2013.01); *G06T 2207/20024* (2013.01); *G06T 2207/20076* (2013.01); *G06T 2207/20224* (2013.01); *G06T 2207/30088* (2013.01); *G06T 2207/30096* (2013.01)

(58) Field of Classification Search
CPC . G06T 2207/10152; G06T 2207/20024; G06T 2207/20076; G06T 2207/20224; G06T 2207/30088; G06T 2207/30096; G06T 5/50; G06T 7/0014; H04N 5/2256; H04N 5/2352

See application file for complete search history.

(56) References Cited

U.S. PATENT DOCUMENTS

| 6,396,949 | B1 | 5/2002 | Nichani | |
|---|---|---|---|---|
| 2002/0128557 | A1* | 9/2002 | Hohla | G01N 21/6486 600/476 |
| 2002/0158971 | A1* | 10/2002 | Daiku | H04N 5/2353 348/226.1 |
| 2003/0081836 | A1* | 5/2003 | Averbuch | G06T 7/215 382/199 |

(Continued)

FOREIGN PATENT DOCUMENTS

CN 103808305 A 5/2014

*Primary Examiner* — Peter D Le
(74) *Attorney, Agent, or Firm* — Innovation Counsel LLP (57) ABSTRACT

An image capturing device used to capture an image of an object is provided. The image capturing device includes a camera, a first light source and a controller. The first light source is disposed adjacent to the camera. The controller is electrically connected to the camera and the first light source and is configured to: control the camera to capture a first picture of the object under the condition that the first light source does not emit any light; control the camera to captures a second picture of the object under the condition that the first light source emits a light; subtract the first picture from the second picture to filter off the background brightness of the second picture to obtain a first filtered picture; and analyze the first filtered picture to obtain a probability of the object matching a certain state.

7 Claims, 7 Drawing Sheets

(56) References Cited

U.S. PATENT DOCUMENTS

| | | | |
|---|---|---|---|
| 2006/0004292 A1* | 1/2006 | Beylin | A61B 5/0084 600/476 |
| 2007/0263099 A1 | 11/2007 | Motta et al. | |
| 2008/0037906 A1* | 2/2008 | Yano | H04N 9/045 382/312 |
| 2008/0094484 A1* | 4/2008 | Wu | H04N 9/735 348/223.1 |
| 2008/0180530 A1* | 7/2008 | Keam | G03B 15/02 348/207.1 |
| 2008/0240606 A1* | 10/2008 | Yamaguchi | G06T 5/005 382/274 |
| 2009/0028461 A1* | 1/2009 | Wieringa | A61B 5/0059 382/284 |
| 2009/0102788 A1* | 4/2009 | Nishida | G06F 3/017 345/158 |
| 2009/0303336 A1* | 12/2009 | Utsugi | G06T 7/11 348/222.1 |
| 2009/0324046 A1* | 12/2009 | Kruger | G06T 7/10 382/131 |
| 2010/0134608 A1* | 6/2010 | Shibasaki | G01N 21/645 348/68 |
| 2010/0194942 A1* | 8/2010 | Wada | G01S 17/48 348/294 |
| 2011/0038544 A1* | 2/2011 | Sekine | G06T 7/90 382/190 |
| 2011/0270092 A1* | 11/2011 | Kang | G01J 3/2823 600/476 |
| 2011/0298909 A1* | 12/2011 | Ando | G06F 3/0304 348/77 |
| 2011/0304719 A1* | 12/2011 | Sekine | G06K 9/00355 348/77 |
| 2012/0106799 A1* | 5/2012 | Shi | G06K 9/3241 382/103 |
| 2012/0140091 A1* | 6/2012 | Irmatov | G06T 7/586 348/222.1 |
| 2012/0224042 A1* | 9/2012 | Saijo | G06T 7/11 348/77 |
| 2013/0038689 A1* | 2/2013 | McDowall | A61B 1/00193 348/45 |
| 2015/0226553 A1* | 8/2015 | Fuchikami | G01C 11/02 348/135 |
| 2015/0227025 A1* | 8/2015 | Park | H05B 45/22 348/224.1 |
| 2015/0374308 A1* | 12/2015 | Tichauer | A61B 5/7278 600/431 |
| 2016/0242657 A1* | 8/2016 | Wang | A61B 5/0261 |
| 2017/0142314 A1 | 5/2017 | Moore et al. | |
| 2018/0220952 A1* | 8/2018 | Lee | A61B 5/743 |

* cited by examiner

IMAGE CAPTURING DEVICE

This application claims the benefit of Taiwan application Serial No. 107118968, filed Jun. 1, 2018, the subject matter of which is incorporated herein by reference.

BACKGROUND OF THE INVENTION

Field of the Invention

The invention relates in general to an image capturing device, and more particularly to an image capturing device capable of obtaining a probability of the object matching a certain state.

Description of the Related Art

When one suspects that he/she might have developed a certain disease, he/she normally goes to see doctor at a hospital and conducts many tests there to obtain a result. He/she may need to spend a large amount of time and money. Therefore, it has become a prominent task for the industries to develop a new technology for detecting the state of the body more efficiently and accurately.

SUMMARY OF THE INVENTION

The present invention provides an image capturing device capable of resolving the above problems.

According to one embodiment of the invention, an image capturing device used to capture an image of an object is provided. The image capturing device includes a camera, a first light source and a controller. The first light source is disposed adjacent to the camera. The controller is electrically connected to the camera and the first light source and is configured to: control the camera to capture a first picture of the object under the condition that the first light source does not emit any light; control the camera to captures a second picture of the object under the condition that the first light source emits a light; subtract the first picture from the second picture to filter off the background brightness of the second picture to obtain a first filtered picture; and analyze the first filtered picture to obtain a probability of the object matching a certain state.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1A:
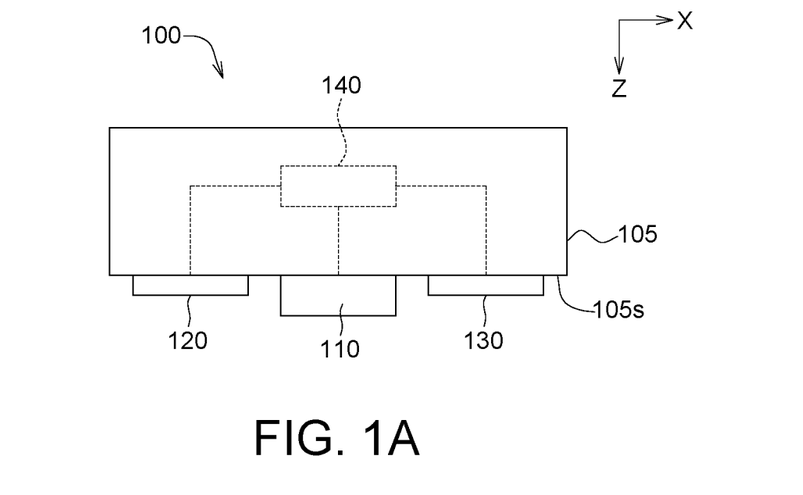
FIGS. 1A and 1B are schematic diagrams of an image capturing device according to an embodiment of the present invention.
Figure 1B:
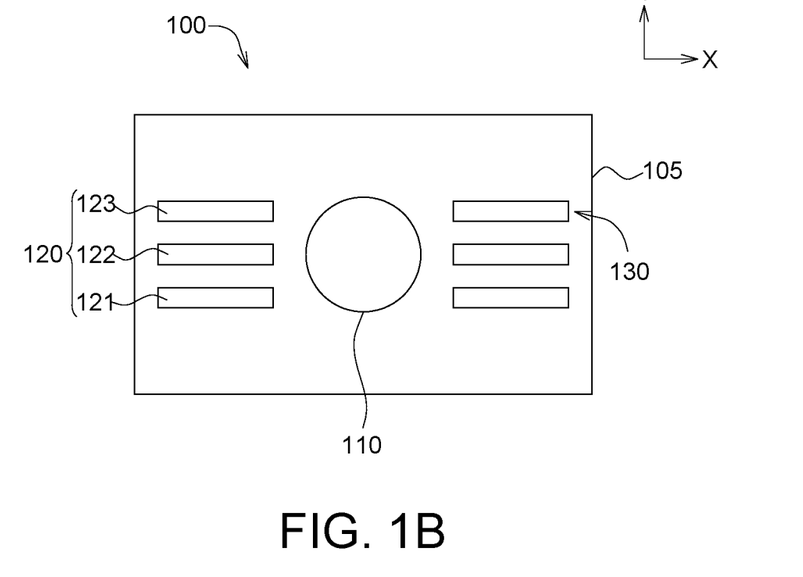

Referring to FIGS. 1A and 1B, schematic diagrams of an image capturing device 100 according to an embodiment of the present invention are shown.

The image capturing device 100 can detect a probability of the object 10 matching a certain state using the technology of optical image analysis. In an embodiment, the object 10 can be a tissue of a biological body (such as a human body or an animal) that can be observed from the appearance. For example, the object 10 can be a susceptible lesion on the skin. The "state" can be a health state of the object 10, such as the degree of cancellation. Specifically, the "state" can be the state of a malignant tumor, a benign tumor or a mole.

The image capturing device 100 advantageously has small volume and convenient portability, and can be used at home. The image capturing device 100 can be used either indoors or outdoors.

As indicated in FIGS. 1A and 1B, the image capturing device 100 includes a camera 110, a first light source 120, a second light source 130 and a controller 140. The first light source 120 and the second light source 130 are disposed adjacent to the camera 110 and are disposed on two opposite sides of the camera 110. For example, the camera 110, the first light source 120 and the second light source 130 are disposed on the same side, such as the surface 105s, of the casing 105 of the image capturing device 100. The controller 140 can be realized by a circuit formed by a semiconductor process, such as a central processing unit (CPU) or other circuit with suitable function. The controller 140 can also be realized by software or firmware.

The first light source 120 and/or the second light source 130 include multiple luminous pieces capable of emitting lights of different primary colors, which can be mixed to form a predetermined color light, such as a white light, a red light or a light of other color. Let the first light source 120 be taken for example. The first light source 120 includes a first luminous piece 121, a second luminous piece 122 and a third luminous piece 123, wherein one of the first luminous piece 121, the second luminous piece 122 and the third luminous piece 123 can emit a red light, another one of the first luminous piece 121, the second luminous piece 122 and the third luminous piece 123 can emit a blue light, and the last one of the first luminous piece 121, the second luminous piece 122 and the third luminous piece 123 can emit a blue light. The red light, the blue light and the green light can be mixed to form a predetermined color light, such as a white light, a red light, or a light of other color. The structure of the second light source 130 is similar to that of the first light source 120, and the similarities are not repeated here. The color of the predetermined color light depends on the variety and/or state of the object, and is not subjected to specific restrictions in the embodiment of the present invention.

Figure 2A:
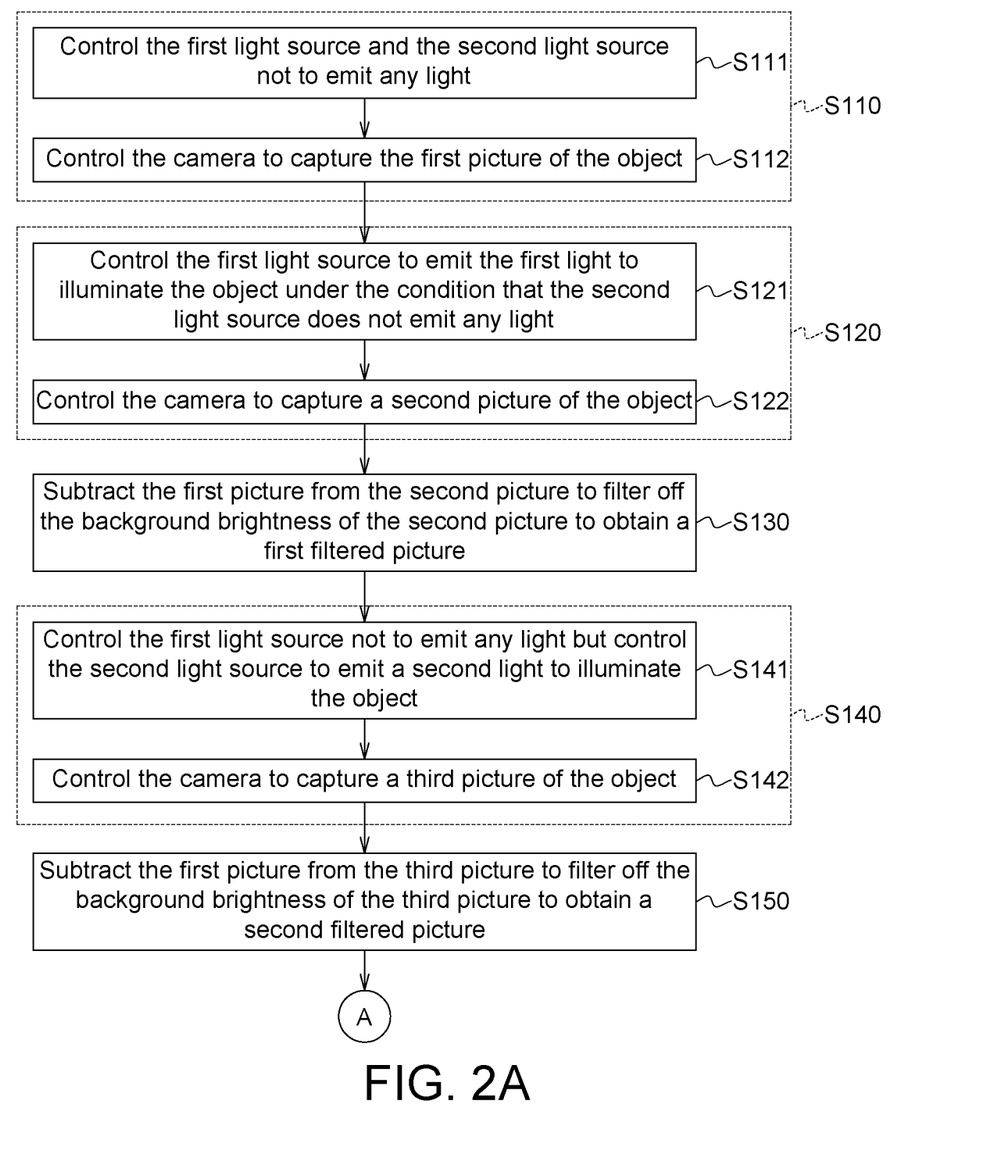
FIGS. 2A and 2B are flowcharts of image analysis using the image capturing device of FIG. 1A.
Figure 2B:
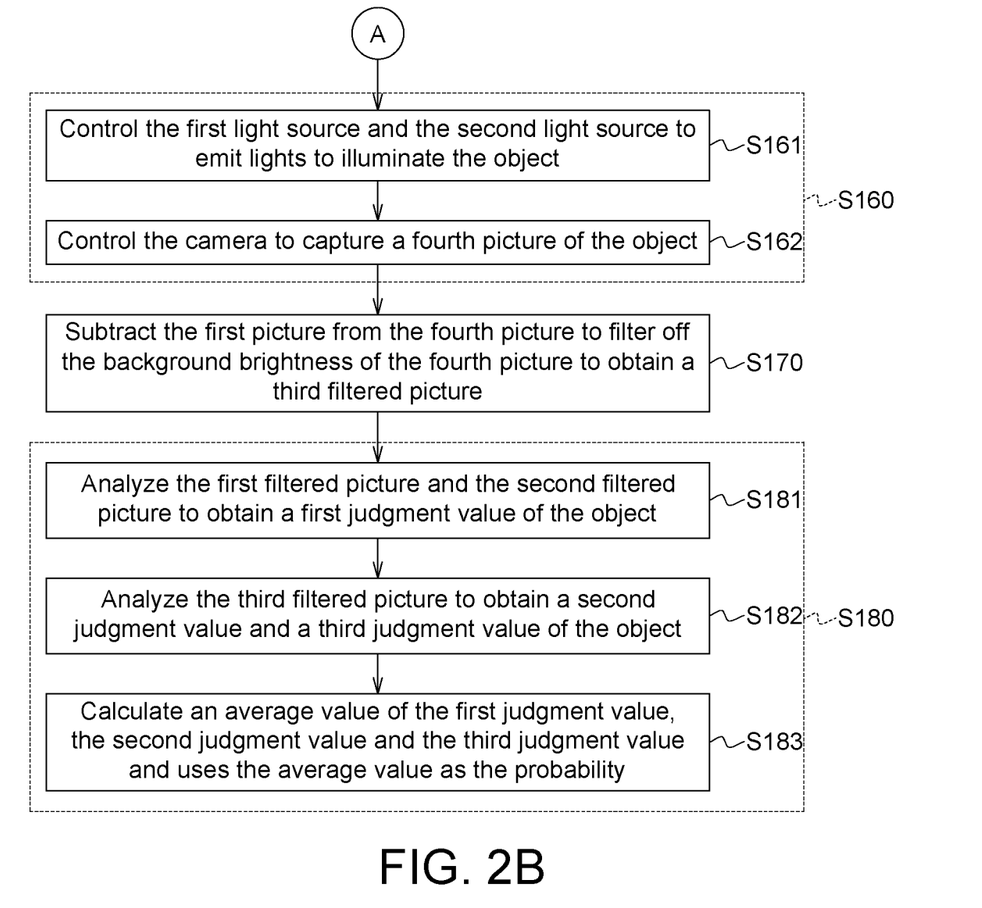

Referring to FIGS. 2A and 2B, flowcharts of image analysis using the image capturing device 100 of FIG. 1A are shown.

Figure 3A:
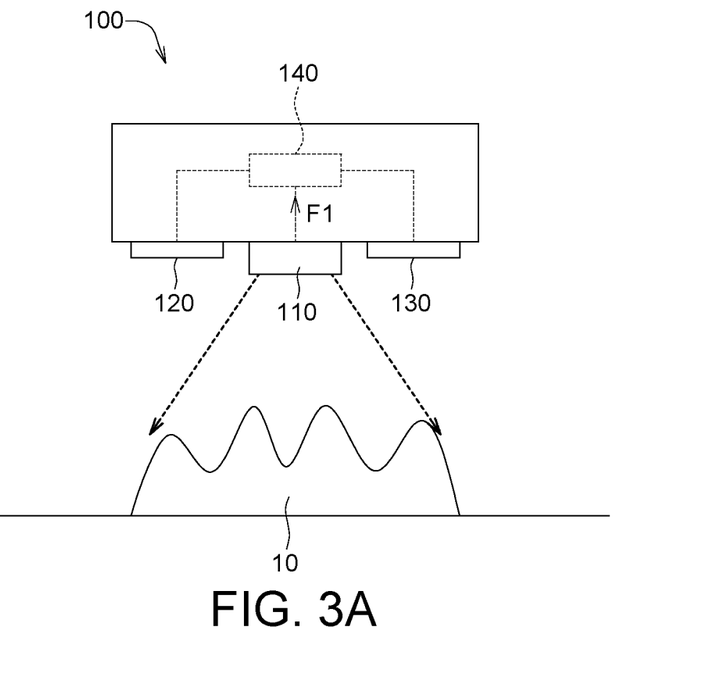
FIG. 3A is a schematic diagram of the image capturing device of FIG. 1A capturing a first picture.
Figure 3B:
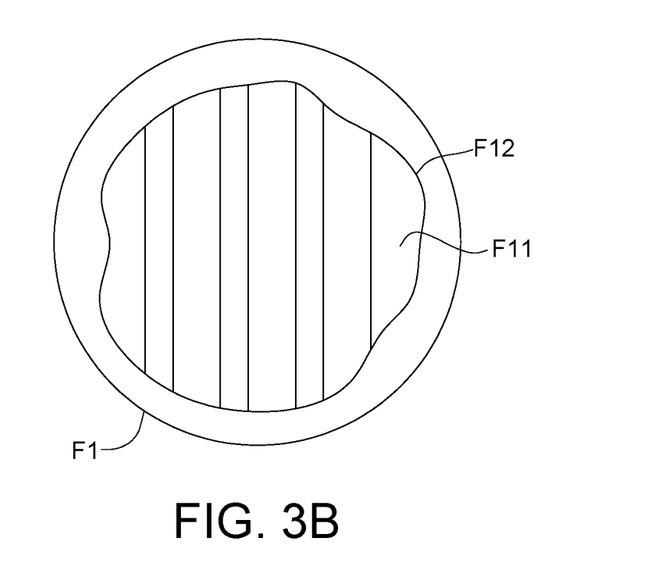
FIG. 3B is a schematic diagram of the first picture captured by the image capturing device of FIG. 3A.

Step S110 is disclosed with reference to FIGS. 3A and 3B. FIG. 3A is a schematic diagram of the image capturing device 100 of FIG. 1A capturing a first picture. FIG. 3B is a schematic diagram of the first picture captured by the image capturing device 100 of FIG. 3A. The controller 140 executes the step of capturing a first picture. For example, the camera 110 is basically aligned with the middle of the object 10, and the controller 140 controls the camera 110 to capture a first picture F1 of the object 10 under the condition that the first light source 120 and the second light source 130 both do not emit any light.

The first picture F1 has an object image F11 under the illumination of a background brightness generated by an ambient light source of the environment where the object 10 is located. The ambient light source is such as a sunlight, a table lamp and/or a fluorescent lamp. As indicated in FIG. 3B, in comparison to the outline F42 of the object image F41 of the fourth picture F4 of FIG. 6B, the outline F12 of the object image F11 of the first picture F1 is less significant because both the first light source 120 and the second light source 130 do not emit any light to illuminate the object 11 in the present step (the outline F12 is drawn using thin lines and is therefore less significant; the outline F42 is drawn using thick lines and is therefore more significant).

Besides, the step S110 may include step S111 and S112. In step S111, the controller 140 controls the first light source 120 and the second light source 130 not to emit any light. In step S112, the controller 140 controls the camera 110 to capture the first picture F1 of the object 10 under the condition that the first light source 120 and the second light source 130 both do not emit any light. In another embodiment, when both the first light source 120 and the second light source 130 do not emit any light, the controller 140 does not need to deliberately control the first light source 120 and the second light source 130 not to emit any light.

Figure 4A:
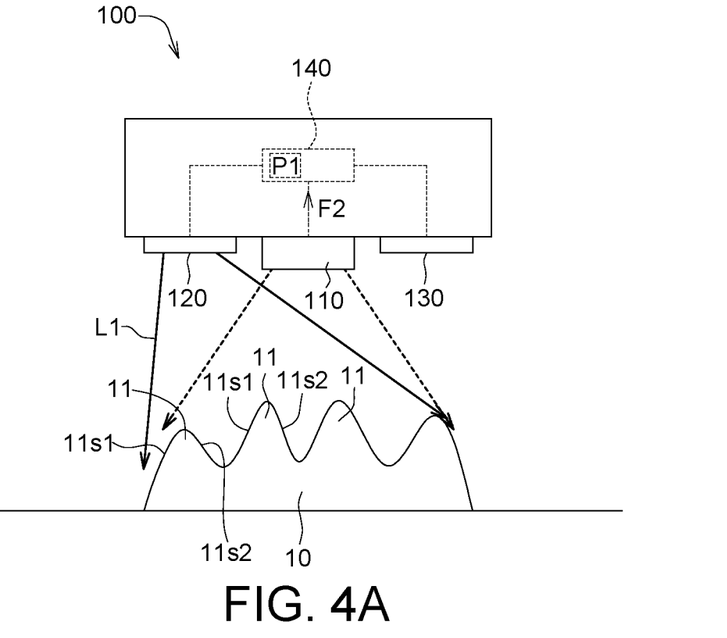
FIG. 4A is a schematic diagram of the image capturing device of FIG. 1A capturing a second picture.
Figure 4B:
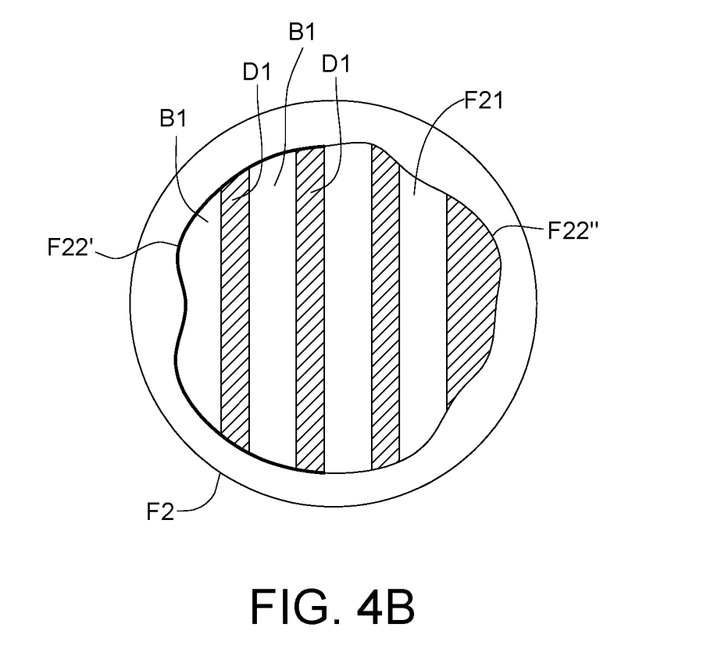
FIG. 4B is a schematic diagram of the second picture captured by the image capturing device of FIG. 4A.

Step S120 is disclosed with reference to FIGS. 4A and 4B. FIG. 4A is a schematic diagram of the image capturing device 100 of FIG. 1A capturing a second picture. FIG. 4B is a schematic diagram of the second picture captured by the image capturing device 100 of FIG. 4A. The controller 140 executes the step of capturing a second picture. For example, the controller 140 controls the camera 110 to capture the second picture F2 of the object 10 under the condition that the first light source 120 emits a light but the second light source 130 does not emit any light. The second picture F2 has an object image F21 under the illumination of the first light source 120.

The step S120 may include step S121 and S122. In step S121, the controller 140 controls the first light source 120 to emit the first light L1 to illuminate the object 10 under the condition that the second light source 130 does not emit any light. In step S122, the controller 140 controls the camera 110 to capture a second picture F2 of the object 10 under the condition that the second light source 130 does not emit any light but the first light source 120 emits the first light L1 to illuminate the object 10.

As indicated in FIG. 4A and FIG. 4B, the object 10 has at least one protrusion 11. The protrusion 11 has a first surface 11s1 and a second surface 11s2 disposed oppositely. Since the camera 110 is basically aligned with the middle of the object 10 and the first light source 120 is located on one side of the camera 110, the first light L1 virtually casts an oblique light on the object 10. Under the condition that the first light L1 casts an oblique light on the object 10, the first surface 11s1 of the protrusion 11 is a light facing surface, and the second surface 11s2 of the protrusion 11 is a backlight surface. The light facing surface has bright regions B1 on the object image F21 of FIG. 4B, and the backlight surface has dark regions D1 on the object image F21. Under the condition that the first light L1 casts an oblique light on the object 10, the outline F22' of the part of the object image F21 of the second picture F2 closer to the first light source 120 becomes more significant than that farther away from the first light source 120 (the outline F22' is drawn using thick lines to indicate that it is relatively significant).

As indicated in FIG. 4B, the distribution of protrusions on the object 10 can be obtained from the distribution of bright/dark regions in the second picture F2. Also, the outline F22' of the relatively significant part of the object 10 can be obtained from the second picture F2. Although it is not illustrated in the diagram, the color distribution of the object 10 can be obtained from the second picture F2.

In step S130, the controller 140 subtracts the first picture F1 from the second picture F2 to filter off the background brightness of the second picture F2 to obtain a first filtered picture P1. Since the first filtered picture P1 has been filtered off the background brightness, the accuracy of image analysis will not be affected by the background brightness. Thus, regardless of the image capturing device 100 being used indoors or outdoors, the influence of the background brightness (such as indoor light, outdoor light or sunlight) can be excluded. Moreover, the terminology "subtract" refers to filtering off a part of optical rendering of the second picture F2 (such as the background brightness). The optical rendering also exists in the first picture F1. The terminology "subtract" used in other paragraphs of the present specification may carry the same or similar meaning, and the similarities are not repeated here.

Figure 5A:
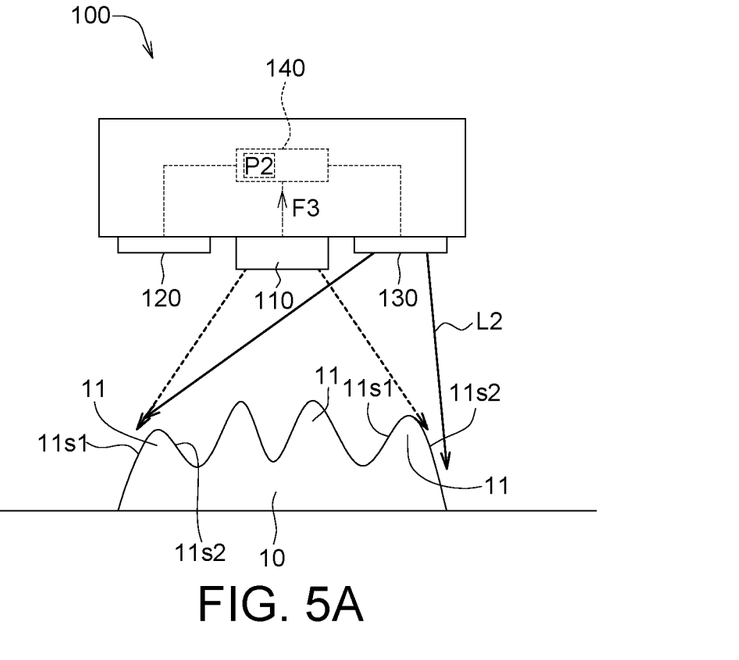
FIG. 5A is a schematic diagram of a third picture captured by the image capturing device of FIG. 1A.
Figure 5B:
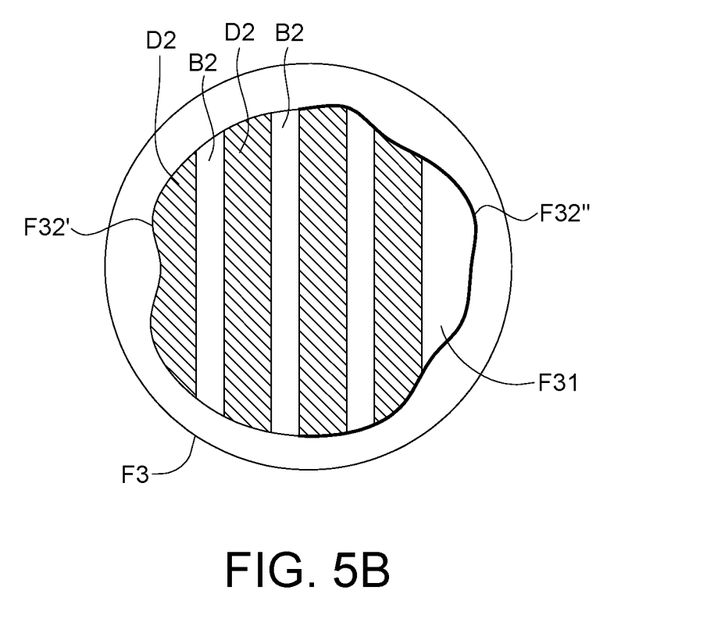
FIG. 5B is a schematic diagram of the third picture captured by the image capturing device of FIG. 5A.

Step S140 is disclosed with reference to FIGS. 5A and 5B. FIG. 5A is a schematic diagram of a third picture captured by the image capturing device 100 of FIG. 1A. FIG. 5B is a schematic diagram of the third picture captured by the image capturing device 100 of FIG. 5A. The controller 140 executes the step of capturing a third picture. For example, the controller 140 controls the camera 110 to capture a third picture F3 of the object 10 under the condition that the first light source 120 does not emit any light but the second light source 130 emits a light to illuminate the object 10. The third picture F3 has an object image F31 under the illumination of the second light source 130 and a background brightness.

Step S140 may include step S141 and S142. In step S141, the controller 140 controls the first light source 120 not to emit any light but controls the second light source 130 to emit a second light L2 to illuminate the object 10. In step S142, the controller 140 controls the camera 110 to capture a third picture F3 of the object 10 under the condition that the first light source 120 does not emit any light but the second light source 130 emits the second light L2.

As indicated in FIG. 5A and FIG. 5B, since the camera 110 is basically aligned with the middle position of the object 10 and the second light source 130 is located on the other side of the camera 110, the second light L2 virtually casts an oblique light on the object 10. Under the condition that the second light L2 casts an oblique light on the object 10, the first surface 11s1 of the protrusion 11 becomes a backlight surface, and the second surface 11s2 of the protrusion 11 becomes a light facing surface. The backlight surface has dark region D2 on the object image F31, and the light facing surface has bright region B2 on the object image F3. Under the condition that the second light L2 casts an oblique light on the object 10, the outline F32" of the part of the object image F31 of the third picture F3 closer to the second light source 130 becomes more significant than that farther away from the second light source 130 (the outline F32" is drawn using thick lines to indicate that it is relatively significant).

As indicated in FIG. 5B, the distribution of protrusions on the object 10 can be obtained from the distribution of bright/dark regions in the third picture F3. Also, the outline F32″ of the relatively significant part of the object 10 can be obtained from the third picture F3. Although it is not illustrated in the diagram, the color distribution of the object 10 can be obtained from the third picture F3. In comparison to the features of the object 10 obtained from only the second picture F2 or the third picture F3, features of the object 10, such as the distribution of protrusions, the distribution of colors and/or the outline of the object 10, are more complete from that obtained from the second picture F2 and the third picture F3 superimposed together.

In step S150, the controller 140 subtracts the first picture F1 from the third picture F3 to filter off the background brightness of the third picture F3 to obtain a second filtered picture P2. Since the second filtered picture P2 has been filtered off the background brightness, the accuracy of image analysis will not be affected by the background brightness.

Figure 6A:
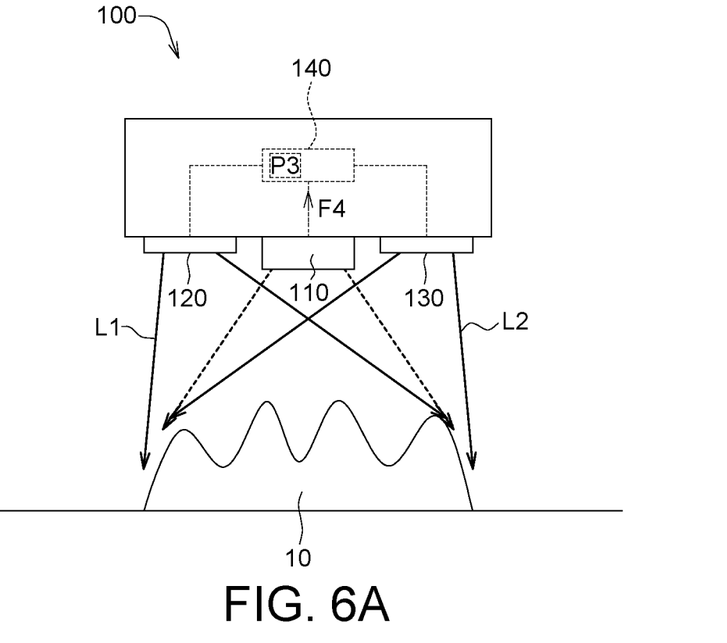
FIG. 6A is a schematic diagram of the image capturing device of FIG. 1A capturing a fourth picture.
Figure 6B:
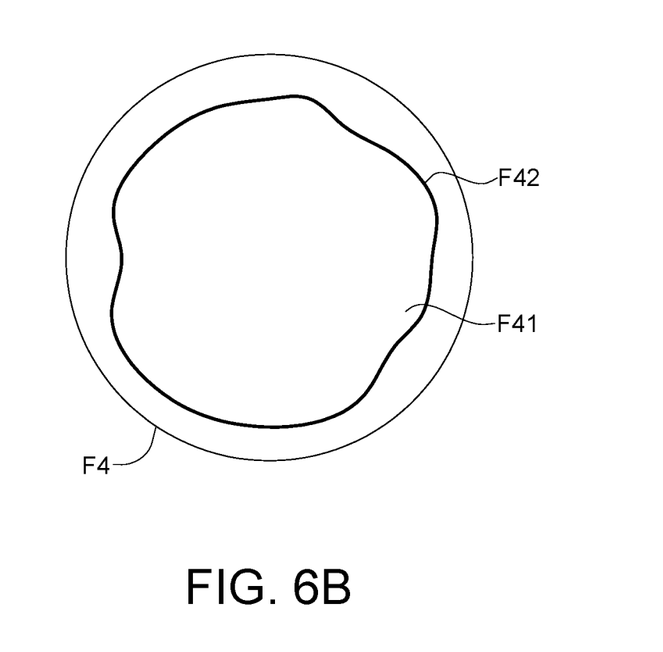
FIG. 6B is a schematic diagram of the fourth picture captured by the image capturing device of FIG. 6A.

Step S160 is disclosed with reference to FIGS. 6A and 6B. FIG. 6A is a schematic diagram of the image capturing device 100 of FIG. 1A capturing a fourth picture. FIG. 6B is a schematic diagram of the fourth picture captured by the image capturing device 100 of FIG. 6A. The controller 140 executes the step of capturing a fourth picture. For example, the controller 140 controls the camera 110 to capture a fourth picture F4 of the object 10 under the condition that the first light source 120 and the second light source 130 both emit a light to illuminate the object 10. The fourth picture F4 has an object image F41 under the illumination of the first light source 120 and the second light source 130 and a background brightness. Since the first light source 120 and the second light source 130 both emit a light to illuminate the object 10, the outline F42 of the object image F41 is relatively significant (in comparison to the outline F12 of the object image F11 of the first picture F1 of FIG. 3B). As indicated in FIG. 6B, the first light source 120 and the second light source 130 both emit a light to illuminate the object 10 and provide a larger brightness (in comparison to the level of brightness in previous steps), therefore the surface unevenness in the object image F41 is less significant and bright/dark regions (the regions corresponding to the protrusions) are omitted in the object image F41 of FIG. 6B. In another embodiment, different levels of significance of the bright/dark regions in the object image F41 can be achieved by controlling the intensities of the first light source 120 and the second light source 130. Examples of the level of significance include "significant", "insignificant" or "not rendered at all", wherein "significant" refers to the level that the first judgment value disclosed below can be achieved.

Step S160 may include step S161 and S162. In step S161, the controller 140 controls the first light source 120 to emit the first light L1 to illuminate the object 10 and controls the second light source 130 to emit the second light L2 to illuminate the object 10. In step S162, the controller 140 controls the camera 110 to capture a fourth picture F4 of the object 10 under the condition that the first light source 120 and the second light source 130 both emit a light to illuminate the object 10.

In step S170, the controller 140 subtracts the first picture F1 from the fourth picture F4 to filter off the background brightness of the fourth picture F4 to obtain a third filtered picture P3. Since the third filtered picture P3 has been filtered off the background brightness, the accuracy of image analysis will not be affected by the background brightness.

In step S180, the controller 140 analyzes the first filtered picture P1, the second filtered picture P2 and the third filtered picture P3 to obtain a probability of the object 10 matching a certain state. Since the first filtered picture P1, the second filtered picture P2 and the third filtered picture P3 all have been filtered off the background brightness, the accuracy of image analysis will not be affected by the background brightness.

In an embodiment, the step S180 may include steps S181-S183.

In step S181, the controller 140 analyzes the first filtered picture P1 and the second filtered picture P2 to obtain a first judgment value of the object 10, wherein the first judgment value can be the degree to which the distribution of the protrusions 11 on the object 10 matches the state. The higher the first judgment value, the larger the probability of the object 10 matching the state.

In step S182, the controller 140 analyzes the third filtered picture P3 to obtain a second judgment value and a third judgment value of the object 10, wherein the second judgment value can be the degree to which the color of the object 10 matches the state, and the third judgment value can be the degree to which the outline of the object 10 matches the state. The larger the first judgment value and the second judgment value, the larger the likelihood that the object 10 matches the state.

In step S183, the controller 140 calculates an average value of the first judgment value, the second judgment value and the third judgment value and uses the average value as the probability. The larger the probability, the larger the likelihood that the object 10 matches the state. Let the state be exemplified by skin cancer. The larger the probability, the more likely that the object 10 is skin cancer (that is, the higher the risk).

In step S180, the controller 140 compares the filtered picture (such as the first filtered picture P1, the second filtered picture P2 and the third filtered picture P3) with multiple feature images of skin cancer to determine or calculate the judgment value (such as the first judgment value, the second judgment value and the third judgment value). Besides, the feature images of skin cancer can be stored in a database (not illustrated) located in the controller 140 or stored in another storage unit, such as an internal memory or an external storage device.

In the present embodiment, the controller 140 concurrently analyzes the first filtered picture P1 and the second filtered picture P2 in step S181, and therefore can obtain the first judgment value with high accuracy. In another embodiment, the controller 140 can analyze only the first filtered picture P1 in step S181 as long as the accuracy of the first judgment value is within a predetermined range. In other embodiments, when the controller 140 analyzes only the first filtered picture P1 in step S181, the image capturing device 100 can selectively omit the second light source 130.

In the present embodiment, since the third filtered picture P3 is obtained under a high intensity of illumination in step S182 (the first light source 120 and the second light source 130 both emit a light to illuminate), the controller 140 can analyze the third filtered picture P3 to obtain the second judgment value and the third judgment value with high accuracy. In another embodiment, the controller 140 can analyze only the first filtered picture P1 in step S182 as long as the accuracy of the second judgment value and the accuracy of the third judgment value are within a predetermined range. In other embodiments, when the controller 140 analyzes only the first filtered picture P1 in step S182, the image capturing device 100 can omit the first light source 120 and the second light source 130.

Furthermore, with the condition that the brightness of the first light source 120 and/or the brightness of the second light source 130 being under suitable control, if the first judgment value, the second judgment value and/or the third judgment value can be obtained from at least one of the first filtered picture P1, the second filtered picture P2 and the third filtered picture P3, then relevant step of obtaining the remaining ones of the first filtered picture P1, the second filtered picture P2 and the third filtered picture P3 can be omitted, and corresponding elements of the image capturing device 100 can be selectively omitted.

Moreover, the embodiment of the present invention does not limit the capturing sequence of the first picture F1, the second picture F2, the third picture F3 and the fourth picture F4; and the first picture F1, the second picture F2, the third picture F3 and the fourth picture F4 can be captured according to any sequence. Also, the embodiment of the present invention does not limit the capturing sequence of the first filtered picture P1, the second filtered picture P2 and the third filtered picture P3; and the first filtered picture P1, the second filtered picture P2 and the third filtered picture P3 can be captured according to any sequence.

While the invention has been described by example and in terms of the preferred embodiment (s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An image capturing device used to capture an image of a biological object, wherein the image capturing device comprises:
    a camera;
    a first light source disposed adjacent to the camera;
    a second light source, wherein the second light source and the first light source are respectively disposed on two opposite sides of the camera; and
    a controller electrically connected to the camera, the first light source and the second light source and configured to:
    control the camera to capture a first picture of the biological object under the condition that the first light source and the second light source both do not emit any light;
    control the camera to capture a second picture of the biological object under the condition that the second light source does not emit any light but the first light source emits a first light to illuminate the biological object;
    control the camera to capture a third picture of the biological object under the condition that the first light source does not emit any light but the second light source emits a second light to illuminate the biological object;
    subtract the first picture from the second picture to filter off the background brightness of the second picture to obtain a first filtered picture;
    subtract the first picture from the third picture to filter off the background brightness of the third picture to obtain a second filtered picture; and
    analyze the first filtered picture and the second filtered picture to obtain a probability of the distribution of a protrusion on the biological object matching a healthy state of the biological tissue.

2. The image capturing device according to claim 1, wherein the image capturing device further comprises a casing, and the camera and the first light source are disposed on the same side of the casing.

3. The image capturing device according to claim 1, wherein the image capturing device allows the first light to cast an oblique light on the biological object.

4. The image capturing device according to claim 1, wherein the image capturing device comprises a casing, and the camera, the first light source and the second light source are all disposed on the same side of the casing.

5. The image capturing device according to claim 1, wherein the image capturing device allows the second light to cast an oblique light on the biological object.

6. The image capturing device according to claim 1, wherein the controller is further used to:
    control the camera to capture an another picture of the biological object under the condition that the first light source and the second light source both emit a light to illuminate the biological object;
    subtract the first picture from the another picture to filter off the background brightness of another picture to obtain an another filtered picture;
    wherein the step of obtaining the probability further comprises: analyzing the first filtered picture, the second filtered picture and the another filtered picture to obtain the probability.

7. The image capturing device according to claim 6, wherein the step of obtaining the probability further comprises:
    analyzing the first filtered picture and the second filtered picture to obtain a first judgment value of the biological object;
    analyzing the another filtered picture to obtain a second judgment value and a third judgment value of the biological object; and
    calculating an average value of the first judgment value, the second judgment value and the third judgment value and using the average value as the probability.

\* \* \* \* \*